United States Patent [19]
Chow et al.

[11] Patent Number: 5,976,120
[45] Date of Patent: Nov. 2, 1999

[54] SINGLE SEGMENT MICROCATHETER

[75] Inventors: Sean L. Chow, Tustin; Donald J. Kolehmainen, Orange; George Robert Green, Jr., Costa Mesa, all of Calif.

[73] Assignee: Micro Therapeutics, Inc., Irvine, Calif.

[21] Appl. No.: 09/048,007

[22] Filed: Mar. 26, 1998

Related U.S. Application Data

[60] Provisional application No. 60/093,063, May 5, 1997.
[51] Int. Cl.$^6$ .................................................. A61M 25/00
[52] U.S. Cl. .......................... 604/525; 604/526; 604/527
[58] Field of Search .................................. 604/525, 526, 604/527, 532

[56] References Cited

U.S. PATENT DOCUMENTS

| | | |
|---|---|---|
| 3,240,233 | 3/1966 | Johnston . |
| 3,935,857 | 2/1976 | Co . |
| 3,948,273 | 4/1976 | Sanders . |
| 4,254,774 | 3/1981 | Boretos . |
| 4,277,432 | 7/1981 | Woinowski . |
| 4,490,421 | 12/1984 | Levy . |
| 4,577,543 | 3/1986 | Wilson . |
| 4,579,555 | 4/1986 | Russo . |
| 4,739,768 | 4/1988 | Engleson . |
| 4,840,623 | 6/1989 | Quackenbush . |
| 4,842,590 | 6/1989 | Tanabe et al. . |
| 4,848,344 | 7/1989 | Sos et al. . |
| 4,876,140 | 10/1989 | Quackenbush . |
| 4,886,506 | 12/1989 | Lovgren et al. . |
| 4,900,314 | 2/1990 | Quackenbush . |
| 4,998,923 | 3/1991 | Samson et al. . |
| 5,085,649 | 2/1992 | Flynn . |
| 5,104,388 | 4/1992 | Quackenbush . |
| 5,104,705 | 4/1992 | Quackenbush . |
| 5,125,913 | 6/1992 | Quackenbush . |
| 5,176,660 | 1/1993 | Truckai . |
| 5,270,086 | 12/1993 | Hamlin . |
| 5,273,536 | 12/1993 | Savas . |
| 5,282,785 | 2/1994 | Shapland et al. . |
| 5,290,306 | 3/1994 | Trotta et al. . |
| 5,308,342 | 5/1994 | Sepetka et al. . |
| 5,312,356 | 5/1994 | Engelson et al. . |
| 5,334,146 | 8/1994 | Ozasa . |
| 5,336,205 | 8/1994 | Zenzen et al. . |
| 5,338,298 | 8/1994 | McIntyre . |
| 5,338,299 | 8/1994 | Barlow . |
| 5,358,493 | 10/1994 | Schweich, Jr. et al. . |
| 5,378,230 | 1/1995 | Mahurkar . |
| 5,411,477 | 5/1995 | Saab . |
| 5,456,674 | 10/1995 | Bos et al. . |
| 5,458,570 | 10/1995 | May, Jr. . |
| 5,474,537 | 12/1995 | Solar . |
| 5,503,631 | 4/1996 | Onishi et al. . |
| 5,525,388 | 6/1996 | Wand et al. . |
| 5,531,715 | 7/1996 | Engelson et al. . |
| 5,533,985 | 7/1996 | Wang . |
| 5,538,512 | 7/1996 | Zenzon et al. . |
| 5,542,937 | 8/1996 | Chee et al. . |
| 5,599,326 | 2/1997 | Carter . |
| B2 4,739,768 | 10/1995 | Engelson . |

FOREIGN PATENT DOCUMENTS

| | | |
|---|---|---|
| 2506106 | 11/1982 | France . |
| 43066136 | 9/1994 | Germany . |
| 1651864 | 5/1991 | Russian Federation . |
| WO 91/07203 | 5/1991 | WIPO . |

*Primary Examiner*—John D. Yasko
*Attorney, Agent, or Firm*—Burns Doane Swecker & Mathis, LLP

[57] ABSTRACT

A single segment catheter has a gradually changing flexibility from a distal to a proximal end of the catheter. According to one embodiment the catheter includes a plurality of strands within the catheter tube wall which change in diameter between the distal and proximal ends to achieve a catheter having a more flexible distal end and a continuously changing flexibility along the catheter length with no joints or distinct changes in flexibility.

24 Claims, 2 Drawing Sheets

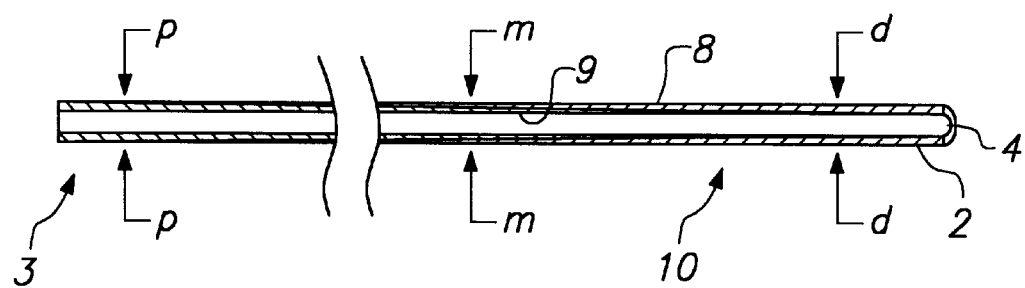
FIG. 11
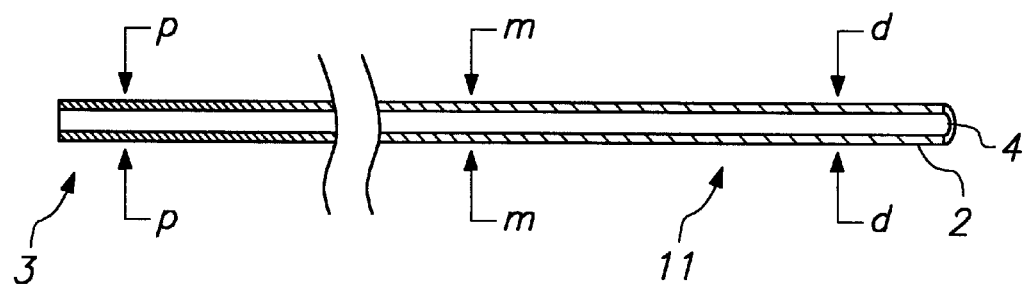
FIG. 12
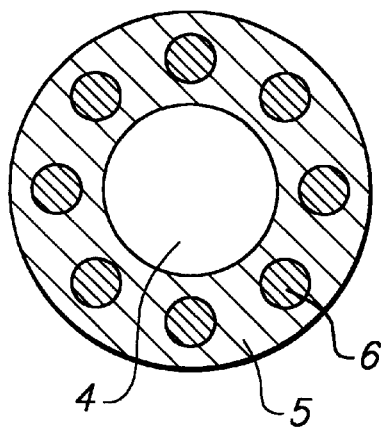 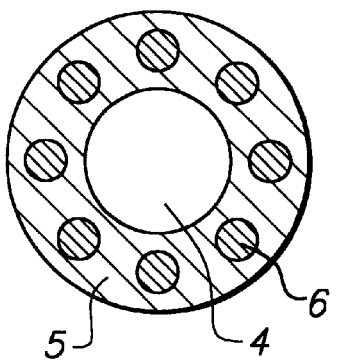 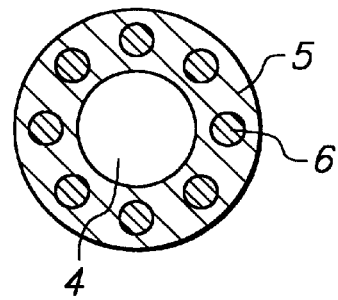
FIG. 15    FIG. 14    FIG. 13

SINGLE SEGMENT MICROCATHETER

RELATED APPLICATIONS

This application claims the benefit under Title 35, United States Code §119(e) of U.S. Provisional Application Ser. No. 60/093,063 filed May 5, 1997.

BACKGROUND OF THE INVENTION

1. Field of the Invention

The invention relates to catheters and more particularly, the invention relates to a microcatheter having a varying flexibility along its length.

2. State of the Related Art

Numerous conditions in the vasculature may be treated or diagnosed with intravascular catheters. Aneurysms, arteriovenous malformations, fistulas and occlusions may be diagnosed with angiography, in which a radiopaque dye is injected into a blood vessel through a catheter while the blood vessel is imaged under fluoroscopy. Stenosis and other occlusive diseases can be diagnosed with ultrasound catheters inserted into the blood vessels. Some vascular maladies, such as occlusions, lesions, tumors, or diseases can be treated with injection of therapeutic agents in the blood vessel through a catheter. Some aneurysms and fistulas may be treated with the injection of embolic materials into the blood vessel. Each of these techniques, and various other techniques, require the insertion of a catheter into the blood vessel. The catheter is preferably inserted into a large remote blood vessel such as the femoral artery and navigated through the vasculature to the target blood vessel.

When the catheters are intended to be inserted into the very small blood vessels of the brain, heart, kidneys, and the like, which are far away from the insertion point and require passage of the catheter through the many twists and turns of the vasculature, guide catheters and/or guide wires are used to help insert the catheter into the target vessel. Typically, a guide wire and catheter are inserted into the femoral artery using the Seldinger technique (or a cutdown). The guidewire can be pushed and twisted to navigate the catheter through the femoral artery, up the descending aorta toward a target site. When accessing the vasculature of the brain, the guidewire and catheter are steered into the aortic arch, then into one of the carotid arteries or vertebral arteries, and then into the brain. Once a tip of the catheter has been placed at the target site, either within the diseased blood vessel or nearby, the guidewire is removed for injection of a therapeutic agent.

The process of tracking becomes more difficult as the guidewire, catheter, and target vessel become very small, and when the target site is deep within the vasculature and involves a highly tortuous path for access. Most small blood vessels of clinical significance must be accessed though highly tortuous pathways. For example, arching over the aortic arch and turning into a coronary artery to reach the distal portion of the coronary arteries, or turning into the carotid arteries or the vertebral arteries, into the Circle of Willis and into the cerebral arteries are common vasculature catheterizations though highly tortuous pathways. To reach a target vessel, the catheter must be quite flexible in order to follow the tortuous path and at the same time, the catheter must be stiff enough to allow the distal end of the catheter to be manipulated from an external access site, which may be as much as one meter or more from the targeted vessels.

In the case of pathological tortuosity, such as when the deep vasculature involves turns in excess of 90° when branching off from one blood vessel to another blood vessel (paths which branch off the preceding vessel at angles greater than a right angle), and where the total path length within the target tissue is at least about 5 cm and is also characterized as being accessible by a guidewire 18 mil or smaller of the type described above, but being too delicate and/or tortuous for accessing by a particularly larger diameter guide wire, the problem is particularly acute.

Placement of catheters in positions deep within the vasculature is quite difficult without the aid of a guide wire, and tracking over a pre-positioned guidewire is often hampered by kinking and columnar collapse of the catheter on the guidewire.

Previous attempts to solve this problem include Engelson, Catheter for Guide-Wire Tracking, U.S. Pat. No. 4,739,768 (Apr. 26, 1988). Engelson proposes the use of a two or three segment catheter where the proximal segment is stiff and the distal segment, which must be at least about 5 cm long, is flexible, and in fact is so flexible that it is incapable of being inserted into a blood vessel without the aid of a guidewire. The catheter is constructed with at least two layers, with the outer layer being more flexible that the inner layer, and extending at least 5 cm past the distal end of the inner layer to form a flexible distal tip should have a gradually increasing stiffness from the distal to the proximal end of the distal segment.

Other methods of controlling the stiffness of different regions of catheter tubes have been proposed. Bos, Catheters with Variable Properties, U.S. Pat. No. 5,456,674 (Oct. 10, 1995) shows a catheter with one or more longitudinal bands of material running the length of the catheter. The bands may be made with differing flexibilities, and the length of each band may be controlled through the operation of cutoff valves during the extrusion manufacturing process. For example, in FIG. 5, Bos illustrates the construction of a multiple segment catheter, where each segment has a band of stiff material, and an intermediate segment of intermediate stiffness has an additional band of stiff material, and the third, stiffest segment has yet two more bands of stiff material.

SUMMARY OF THE INVENTION

The catheter according to one aspect of the present invention has a gradually increasing wall thickness from the distal tip to the proximal end. The catheter is made of a suitable medical grade plastic such as low density polyethylene. The catheter also has at least one strand of differing stiffness embedded within the wall of the catheter, and this strand may be made of another suitable plastic such as high density polyethylene. The thickness of the strands is varied along the length of the catheter to provide a catheter with a single segment which varies in flexibility from the distal end to the proximal end, with the distal end being extremely flexible so that it easily tracks along a guidewire, and the proximal end becoming increasing stiff so that it has suitable columnar strength and provides adequate pushability.

Other embodiments of the present invention provide for gradual increase in flexibility from the proximal end of the catheter to the distal end or, conversely, gradual increase in stiffness of the catheter from the distal end to the proximal end. In each of these constructions, the provision of a catheter with a single segment, with no discrete changes in the flexibility of the catheter, provides the advantages of a catheter which can track along a guidewire into highly tortuous pathways without the kinking and pushability problems of catheters using two or more segments of different flexibility.

According to another aspect of the present invention, a single segment catheter includes a catheter tube having a proximal end and a distal end, said catheter tube having a catheter tube wall defining a lumen extending from the proximal end to the distal end, and at least one strand within the tube wall, said strand extending substantially from the proximal end to the distal end of the catheter tube, said strand having a changing diameter from the proximal end the distal end of the catheter, said strand comprising a material having a stiffness different from a stiffness of the material of the catheter tube.

BRIEF DESCRIPTION OF THE DRAWINGS

The invention will be described in greater detail with reference to the preferred embodiments illustrated in the accompanying drawings, in which like elements bear like reference numerals, and wherein:

FIG. 11 is a longitudinal cross sectional view of the catheter with a two layer construction;

FIG. 12 is a longitudinal cross sectional view of a catheter according to a fourth embodiment with a material gradient construction;

FIG. 13 is a radial cross section of a distal portion of the catheter according to a fifth embodiment;

FIG. 14 is a radial cross section of a midsection of the catheter according to the fifth embodiment; and FIG. 15 is a radial cross section of a proximal portion of the catheter according to the fifth embodiment.

DETAILED DESCRIPTION OF THE PREFERRED EMBODIMENTS

Figure 1:
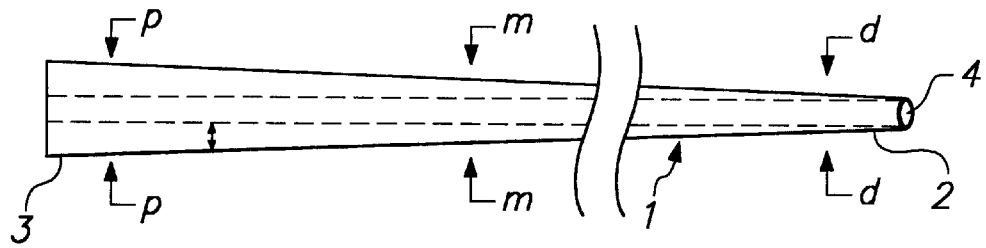
FIG. 1 is a perspective view of the catheter according to one aspect of the present invention.

FIG. 1 shows a catheter 1 according to one aspect of the present invention with a small diameter distal end 2, a relatively larger diameter proximal end 3, and a lumen 4 extending from the distal end to the proximal end of the catheter. The catheter 1 includes one of the stiffening mechanisms illustrated in the embodiments of FIGS. 2–12 which varies the stiffness of the catheter along the length of the catheter resulting in varying properties at different locations along the catheter without discrete changes in flexibility of the catheter. Preferably the catheter has a relatively flexible distal end for use in following the course of a blood vessel and a proximal portion of a more rigid construction to convey pressure exerted on the proximal portion to the distal portion.

According to a first embodiment shown in FIGS. 1–4, the outer diameter of the catheter 1 increases gradually from the distal end 2 to the proximal end 3, and the inner lumen 4 preferably has a substantially constant diameter X along its entire length. The inner lumen 4 may be enlarged near the proximal end 3 to make it easier to load the guidewire. The inner lumen diameter X is about 0.010 to 0.020 inches (0.254–0.508 mm) to accommodate and closely fit standard guidewires which are commonly available in 0.012, 0.014, 0.018 inch sizes, as well as other sizes, and smaller sizes are expected to become standard. The outer diameter of the catheter will be just slightly larger than the lumen diameter, at approximately 0.025 to 0.032 inches (0.635–0.813 mm) at the distal end and gradually increasing to about 0.030 to 0.040 inches (0.762 mm to 1.016 mm), preferably about 0.035 inches (0.889 mm) at the proximal end. The overall length of the catheter may vary from about 60 cm or less to 175 cm or more, depending on the application.

Figure 4:
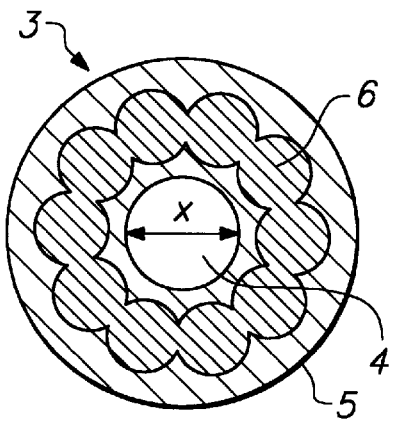
FIG. 4 is a radial cross section of a proximal portion of the catheter according to the first embodiment.
Figure 3:
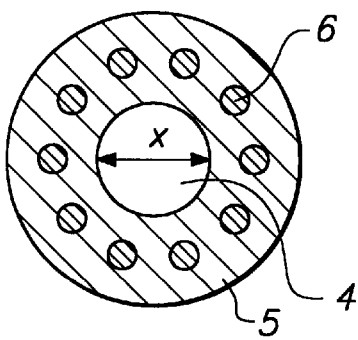
FIG. 3 is a radial cross section of a midsection of the catheter according to the first embodiment.
Figure 2:
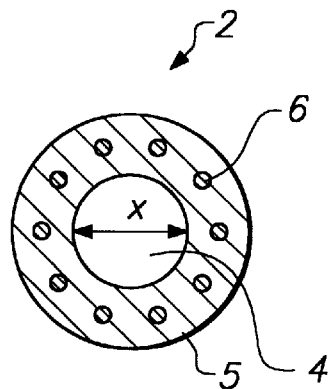
FIG. 2 is a radial cross section of a distal portion of the catheter according to a first embodiment.

The stiffening mechanism in the embodiment of FIGS. 1–4 includes at least one and preferably a plurality of strands 6. The distal cross section corresponding to line dd of FIG. 1 is shown in FIG. 2. As shown in FIG. 2, the catheter wall material 5 comprises most of the overall cross section at the distal end. The strands 6 at the distal end are small relative to the cross sectional wall thickness. In fact, the strands 6 may taper away completely and disappear at the distal end portion 2 of the catheter. A flexible distal tip without any strands may be as long as about 30 cm. The inner diameter X, as mentioned above, may vary depending on the size of the guidewire which will be used with the catheter. In FIG. 3, which shows the radial cross section of a midsection of the catheter along line mm, the quantity of catheter wall material 5 and the catheter wall thickness is slightly larger than that at the distal end 2 of the catheter. The strands 6 at the midsection are also slightly larger than at the distal end. In FIG. 4, the radial cross section of the proximal end of the catheter along line pp, is shown in which the catheter wall thickness is still larger than at the midsection of the catheter, and the strands 6 are also larger. The strands 6 may become so large that they fuse together to form an intramural ring within the catheter wall 5.

The materials used for both the catheter wall 5 and the strands 6 are preferably polymers including thermoplastics, such as, polyethylene (LDPE or HDPE), polypropylene, polystyrene, polyurethanes, polyesters (Nylon), polyfluorocarbons, polyolefin, as well as composite materials, blends, and copolymers thereof. Preferably the catheter strands 6 are formed of a material with a stiffness greater that a material of the catheter wall 5. These two materials are preferably miscible, such that the strands 6 will melt into the catheter body 5 when extruded and form a body without distinct boundaries between the strands 6 and the wall 5.

One exemplary embodiment of the catheter includes a catheter wall made of low density polyethylene (LDPE) and polyolefin (ethylene octane) in approximately equal portions and strands made of a higher stiffness material, such as, high density polyethylene (HDPE). The materials used in the catheter may vary according to the intended use, and many other plastics and composite materials, and even metals, may be used. For example, the catheter wall may comprise LDPE, and the strands may comprise HDPE, LDPE, or a mixture of the two.

According to an alternative embodiment of the invention, the relative stiffness of the materials may be reversed, with the catheter wall 5 comprising the stiffer material, and the strands 6 comprising the more flexible material. In this case the strands 6 will be thicker at the distal end and thinner at the proximal end to provide a catheter with increasing flexibility distally.

Figure 7:
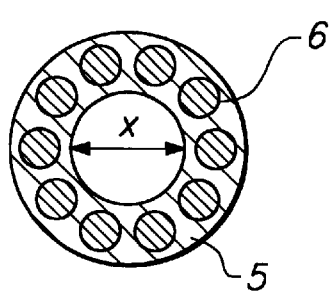
FIG. 7 is a radial cross section of a proximal section of the catheter according to the second embodiment.
Figure 6:
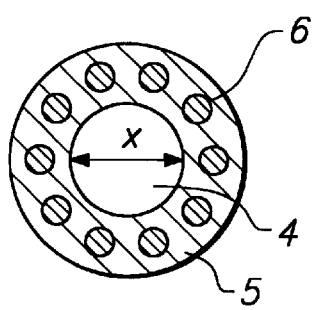
FIG. 6 is a radial cross section of a midsection of the catheter according to the second embodiment.
Figure 5:
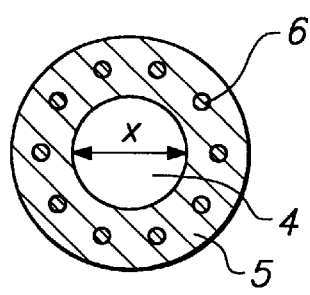
FIG. 5 is a radial cross section of a distal portion of the catheter according to a second embodiment.

FIGS. 5, 6 and 7 show the distal, midsection, and proximal cross sections of a second embodiment of the catheter. The strands increase in thickness from the distal cross section dd of FIG. 5 to the proximal cross section pp of FIG. 7, but the outer diameter of the catheter remains substantially constant along the entire length of the catheter. The inner diameter X also remains substantially constant along the length of the catheter. Accordingly, as the quantity of strand material decreases from the proximal end 3 to the distal end 2, the quantity of catheter wall material 5 increases by approximately the same quantity.

Figure 10:
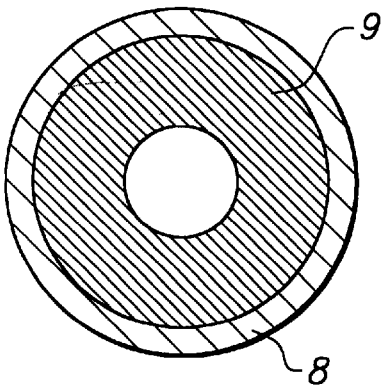
FIG. 10 is a radial cross section of a proximal portion of the catheter according to the third embodiment.
Figure 9:
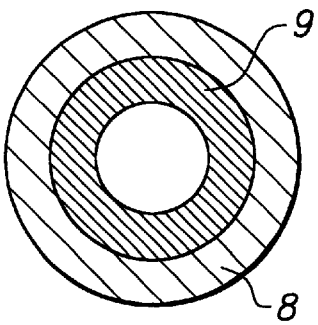
FIG. 9 is a radial cross section of a midsection of the catheter according to the third embodiment.
Figure 8:
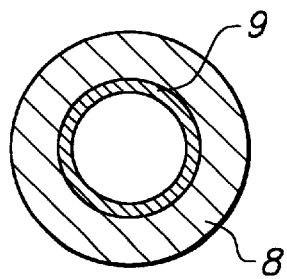
FIG. 8 is a radial cross section of a distal portion of a catheter according to a third embodiment.

FIGS. 8, 9 and 10 show distal, midsection, and proximal cross sections of the third embodiment of the catheter, along cross sections dd, mm, and pp respectively. Rather than using strands of increasing thickness proximally, this embodiment uses an inner layer 9 having a gradually increasing thickness proximally. The outer layer 8 in this embodiment is the more flexible of the two layers, and the inner layer 9 is the stiffer of the two layers. The outer layer 8 comprises, for example, LDPE or a mix of LDPT and polyolefin, and the inner layer 9 comprises for example, HDPE. Comparison of the thickness of the inner layer 9 shown in each of FIGS. 8, 9, and 10 show that the inner layer becomes gradually thicker and comprises a larger portion of the wall thickness from the distal cross section dd to the proximal cross section pp. FIG. 11 illustrates the longitudinal cross section of a catheter 10 corresponding to the three radial cross sections of FIGS. 8, 9, and 10, where the thickness of inner layer 9 gradually increases from the distal end 2 to the proximal end 3. This catheter may have a substantially uniform outer diameter along its entire length, or it may have an increasing outer diameter toward the proximal end. The distal end 2 may include a segment where the inner layer 9 is completely absent and the catheter is formed of only the outer layer 8.

FIG. 12 shows a fourth embodiment of the invention in which the structure of the catheter which provides the gradually increasing stiffness along the length of the catheter is non-discrete, meaning that no discrete strands are present in the catheter wall. Instead, the composition of the catheter gradually changes along the length of the catheter from one material to the next. The distal end of the catheter is formed of a more flexible material, for example LDPE, and the proximal end of the catheter is formed mainly of a less flexible material such as HDPE. In between the distal and proximal end, the catheter composition gradually changes from one material to another, i.e., from predominantly LDPE to predominantly HDPE. The stippling shown in the cross section indicates the gradual transition of the catheter wall from LDPE to HDPE.

The several embodiments described above illustrate the construction of a single segment catheter which has increasing stiffness from the distal end of the catheter to the proximal end of the catheter. Each of the catheters have only one segment with non-discernible discrete change in flexibility along the length of the catheter. In practice, the catheters will most likely incorporate a radiopaque marker at or near the distal tip and a proximal hub such as a luer fitting for connection to injection sources. A strain relief may be included at the connection between the proximal hub and the proximal end of the catheter.

The catheter of the present invention is designed for use in the highly tortuous blood vessels of the body, including the coronary blood vessels, renal blood vessels, and intracranial blood vessels. Highly tortuous, is intended to describe the typical tortuosity encountered in the vascular pathway from a remote access site such as the femoral artery to target sites deep within the coronary, renal sinus and cerebral vasculature. Specific embodiments may be constructed for access into targeted sites involving pathologically tortuous blood vessels. The term pathological tortuosity is intended to describe the vascular pathway from a remote access site such as the femoral artery to target sites involving turns in excess of 90° when branching off from one blood vessel to another blood vessel (paths which branch off the preceding vessel at angles greater that a right angle), and the total path length within the target tissue is at least about 5 cm and is also characterized as being accessibly by a guidewire 18 mil (0.046 mm) or smaller, but being too delicate and/or tortuous for accessing by a significantly larger-diameter guide-wire. The use of the term catheter is intended to include both catheters and microcatheters.

In use, the catheter will normally be used in conjunction with a guidewire, but a guidewire is not always needed. The flexibility of the device may be varied to permit the catheter to be guided into the targeted site in a flow directed manner, or through manual steering. The materials and dimensions described above may be varied so that for use in highly tortuous pathways, use of the catheter with or without a guidewire may be accomplished at the discretion of the operating physician.

The catheters may be manufactured using various known extrusion methods. Known methods of co-extrusion, including cross header arrangements, over-extrusion, and extrusion die construction may be applied to manufacture these catheters. Strand thickness, wall thickness, and relative percentage of composition can be controlled with known techniques including speed controlled extrusion, throttled flow controlled extrusion, waste-gating and other known methods. The several materials mentioned for use in the catheters have proven useful, but it is expected that new and better materials will be applied in the construction of the inventions described above.

The catheter may be manufactured by a first extrusion method in which the tubular catheter having a plurality of strands is co-extruded from a first material forming the catheter wall and a second material forming the strands. The diameter of the strands is varied during the extrusion process to form a catheter having a changing flexibility along its length.

According to an alternative embodiment of the invention, the catheter may be extruded as a tubular member having a constant cross-sectional configuration including a first wall material and a second strand material. The extruded tubular member having a constant cross-sectional configuration is then heated and stretched to the final configuration in which the distal end is smaller in diameter and more flexible than the proximal end. The cross sections of a distal, medial, and proximal portion of a catheter formed by this method are illustrated in FIGS. 13, 14, and 15, respectively. As shown in the figures, as the catheter is stretched, the strands 6 decrease in diameter and move closer together. The inner and outer diameters of the catheter decreases toward the distal tip. In fact, the strands 6 may contact one another and melt together into a ring of strand material at the distal end as the catheter is stretched.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

What is claimed is:

1. A single segment catheter having changing flexibility along the length of the catheter comprising:
   a catheter tube having a proximal end and a distal end, said catheter tube having a catheter tube wall defining a lumen extending from the proximal end to the distal end; and
   at least one strand within the tube wall, said at least one strand extending substantially from the proximal end to the distal end of the catheter tube, said at least one strand having a changing diameter from the proximal end to the distal end of the catheter tube and having a stiffness different from a stiffness of the material of the catheter tube.

2. The single segment catheter according to claim 1, wherein the lumen of the catheter tube has a diameter which accommodates a guidewire and permits tracking of the catheter tube with the guidewire.

3. The single segment catheter according to claim 1, wherein the at least one strand includes a plurality of strands which change in diameter from the proximal end to the distal end of the catheter tube at the same rate.

4. The single segment catheter according to claim 1, wherein the at least one strand is completely encapsulated by the material of the catheter tube.

5. The single segment catheter according to claim 1, wherein the diameter of the at least one strand decreases from the proximal end to the distal end of the catheter tube and the material of the at least one strand has a stiffness greater than the stiffness of the material of the catheter tube.

6. The single segment catheter according to claim 1, wherein an outer diameter of the catheter tube increases from the distal end to the proximal end of the catheter tube.

7. The single segment catheter according to claim 1, wherein an outer diameter of the catheter tube is substantially constant from the distal end to the proximal end of the catheter tube.

8. The single segment catheter according to claim 1, wherein the at least one strand includes a plurality of strands which are distinct at the distal end and are melted together at the proximal end of the catheter tube.

9. The single segment catheter according to claim 1, wherein the plurality of strands taper away completely at the distal end of the catheter tube such that the distal end has no strands present.

10. A method of forming a single segment catheter having a changing flexibility along a length of the catheter, the method comprising:
    extruding a tubular member having a catheter wall formed of a first material and a plurality of strands formed of a second material and surrounded by the first material; and
    varying the diameter of the plurality of strands during extrusion of the tubular member to form a catheter having a changing flexibility along a length of the catheter.

11. The method of forming a single segment catheter according to claim 10, wherein the second material has a stiffness greater than the first material.

12. The method of forming a single segment catheter according to claim 10, wherein an outer diameter of the tubular member remains substantially constant during extrusion.

13. The method of forming a single segment catheter according to claim 10, wherein an outer diameter of the tubular member changes during extrusion.

14. The method of forming a single segment catheter according to claim 10, wherein the second material of the plurality of strands is completely encapsulated by the extruded second material of the catheter wall.

15. The method of forming a single segment catheter according to claim 10, wherein the first material of the catheter wall and the second material of the plurality of strands are melted together during extrusion to form a catheter without distinct boundaries between the catheter wall and the plurality of strands.

16. A method of forming a single segment catheter having a changing flexibility along a length of the catheter, the method comprising:
    extruding a tubular member having a wall formed of a first material and a plurality of strands formed of a second material;
    heating the extruded tubular member; and
    stretching the heated tubular member to form a catheter having a changing flexibility along a length of the catheter.

17. The method of forming a single segment catheter according to claim 16, wherein the strands are surrounded by the first material of the wall.

18. The method of forming a single segment catheter according to claim 16, wherein the second material has a stiffness greater than the first material.

19. The method of forming a single segment catheter according to claim 16, wherein the step of heating is performed by steam heating.

20. The single segment catheter according to claim 1, wherein the strands are indiscrete.

21. The single segment catheter according to claim 1, wherein the at least one strand is formed of HDPE and the material of the catheter tube is LDPE.

22. The method of forming a single segment catheter according to claim 15, wherein the first material of the catheter wall is LDPE and the second material of the plurality of strands is HDPE.

23. A single segment catheter having a changing flexibility along a length of the catheter comprising:
    a catheter tube having a proximal end and a distal end, the composition of the catheter gradually changing from LDPE at the distal end to HDPE at the proximal end to provide a catheter tube having a stiffness at the distal end which is less than a stiffness at the proximal end.

24. A single segment catheter according to claim 23, wherein an external diameter of the catheter tube is substantially constant between the distal end and the proximal end.

* * * * *